US011815209B2

(12) United States Patent
Feith et al.

(10) Patent No.: US 11,815,209 B2
(45) Date of Patent: *Nov. 14, 2023

(54) SPIGOT TUBE COUPLER WITH BONDING AGENT GROOVE

(71) Applicant: CareFusion 303, Inc., San Diego, CA (US)

(72) Inventors: Raymond P. Feith, Chino Hills, CA (US); Randy Kipp, Upland, CA (US); Soon Y. Park, Cypress, CA (US); Siddarth K. Shevgoor, Mission Viejo, CA (US)

(73) Assignee: CAREFUSION 303, INC., San Diego, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 18/112,901

(22) Filed: Feb. 22, 2023

(65) Prior Publication Data
US 2023/0194029 A1 Jun. 22, 2023

Related U.S. Application Data

(63) Continuation of application No. 17/482,757, filed on Sep. 23, 2021, now Pat. No. 11,614,189.

(60) Provisional application No. 63/112,042, filed on Nov. 10, 2020.

(51) Int. Cl.
F16L 33/34 (2006.01)
(52) U.S. Cl.
CPC .................................. F16L 33/34 (2013.01)
(58) Field of Classification Search
CPC ................................ F16L 33/34; A61M 39/12

USPC ........................................................ 285/256
See application file for complete search history.

(56) References Cited

U.S. PATENT DOCUMENTS

| 1,778,244 | A | * | 10/1930 | Cadden ................... B25B 27/10 |
| | | | | 285/259 |
| 2,139,745 | A | | 12/1938 | Goodall |
| 3,017,203 | A | | 1/1962 | Keith |
| 4,256,333 | A | | 3/1981 | Jones |
| 4,330,142 | A | | 5/1982 | Paini |
| 4,703,957 | A | | 11/1987 | Blenkush |
| 4,776,849 | A | | 10/1988 | Shinno et al. |
| 5,165,733 | A | | 11/1992 | Sampson |
| 5,171,046 | A | | 12/1992 | Iwata |
| 5,556,136 | A | | 9/1996 | Von Berg |
| 5,797,627 | A | | 8/1998 | Salter |
| 5,823,580 | A | | 10/1998 | Ungerecht |
| 5,853,202 | A | | 12/1998 | Li |

(Continued)

OTHER PUBLICATIONS

International Search Report and Written Opinion for Application No. PCT/US2021/058444, dated Mar. 1, 2022, 13 pages.

Primary Examiner — David Bochna
(74) Attorney, Agent, or Firm — Morgan, Lewis & Bockius LLP

(57) ABSTRACT

Spigot tube couplers for fluid flow sets and devices are provided. The spigot tube coupler includes a stop surface and a spigot extending from the stop surface and configured to be inserted into a tube. The spigot includes an insertion end, a fluid port, an outer surface, a collar and a plurality of grooves disposed around the outer surface. The plurality of grooves are configured to receive a bonding agent to provide a plurality of bonding areas between the spigot and the tube. Methods for assembling a spigot tube coupler and a tube are also provided.

17 Claims, 6 Drawing Sheets

(56) References Cited

U.S. PATENT DOCUMENTS

| | | | |
|---|---|---|---|
| 6,419,278 B1* | 7/2002 | Cunningham | F16L 33/2071 |
| | | | 285/256 |
| 7,014,214 B2 | 3/2006 | Kaneko | |
| 8,287,007 B2 | 10/2012 | Reiter | |
| 10,107,430 B2 | 10/2018 | Birkholz | |
| 10,436,354 B1 | 10/2019 | Currey | |
| 11,614,189 B2* | 3/2023 | Feith | A61M 39/12 |
| | | | 285/1 |
| 2004/0227344 A1* | 11/2004 | Lin | F16L 33/2071 |
| | | | 285/259 |
| 2008/0197624 A1 | 8/2008 | Nakano | |
| 2010/0084860 A1 | 4/2010 | Cariccia | |
| 2011/0315299 A1 | 12/2011 | Eckardt | |
| 2012/0169041 A1 | 7/2012 | King | |
| 2013/0009394 A1 | 1/2013 | Chaloupka | |
| 2015/0226356 A1 | 8/2015 | Kury | |
| 2015/0335873 A1 | 11/2015 | Khalaj | |
| 2016/0003391 A1 | 1/2016 | Okita | |
| 2016/0151620 A1 | 6/2016 | Blake | |
| 2017/0021561 A1 | 1/2017 | Mezzalira | |
| 2019/0231969 A1 | 8/2019 | Hougaard et al. | |
| 2020/0316358 A1 | 10/2020 | Feith | |
| 2021/0353855 A1 | 11/2021 | Suwito | |

\* cited by examiner

SPIGOT TUBE COUPLER WITH BONDING AGENT GROOVE

CROSS-REFERENCES TO RELATED APPLICATIONS

This Application is a continuation of U.S. patent application Ser. No. 17/482,757 entitled "SPIGOT TUBE COUPLER WITH BONDING AGENT GROOVE," filed on Sep. 23, 2021, and issued as U.S. Pat. No. 11,614,189 on Mar. 8, 2023, which claims the benefit of U.S. Provisional Patent Application No. 63/112,042 entitled "SPIGOT TUBE COUPLER WITH BONDING AGENT GROOVE," filed on Nov. 10, 2020, the disclosure of each which is hereby incorporated by reference in its entirety for all purposes.

BACKGROUND

Spigot tube couplers are used in the medical field in devices for controlling fluid flow to a patient, such as for fluid flow from an intravenous (IV) gravity or pump set. Typical spigot tube couplers do not provide enough tubing retention force when glue is applied to the outside of the spigot and assembled into a tube due to lack of a glue layer that bonds the tubing to the spigot surface. As the spigot is pushed into the tube, the glue on the outside surface of the spigot tends to be wiped off of the spigot and ooze out of the spigot/tube connection due to the friction fit between the spigot and the tube. It is desirable to provide a spigot tube coupler that provides bonding layers between the tube and the spigot surface, thus increasing the tube retention strength of the spigot/tube connection.

SUMMARY

The present disclosure provides medical spigot tube couplers having one or more grooves disposed on the spigot outside surface, increasing the surface area of the spigot and yielding more bonding agent surface area than the typical spigot design.

In one or more embodiments, a spigot tube coupler is provided. The spigot tube coupler includes a housing having a first fluid port disposed at a first end of the housing and a stop surface disposed at a second end of the housing. The spigot tube coupler includes a spigot extending from the stop surface and configured to be inserted into a tube. The spigot includes an insertion end, a second fluid port disposed at the insertion end, an outer surface, a collar disposed at the insertion end of the spigot, the collar having an outer diameter greater than the outer surface of the spigot and the outer surface having a continuous diameter between the stop surface and the collar, and one or more grooves disposed around the outer surface. The one or more grooves are configured to receive a bonding agent to provide one or more bonding layers between the spigot and the tube.

In one or more embodiments, a spigot tube coupler is provided. The spigot tube coupler includes a stop surface having a base member and a spigot extending from the base member and configured to be inserted into a tube. The spigot includes an insertion end, a fluid port disposed in the center of the spigot, an outer surface, a collar disposed at the insertion end of the spigot, the collar having an outer diameter greater than the outer surface of the spigot and the outer surface having a continuous diameter between the base member and the collar, and a plurality of grooves disposed around the outer surface. The plurality of grooves are configured to receive a bonding agent to provide a plurality of bonding areas between the spigot and the tube.

In one or more embodiments, a method of assembling a spigot tube coupler and a tube is provided. The method includes applying a bonding agent to an outer surface of a spigot of a spigot tube coupler, the spigot comprising a plurality of grooves disposed around the outer surface, the outer surface having a continuous diameter between a stop surface of the spigot tube coupler and a collar disposed at an insertion end of the spigot. The method also includes aligning an insertion end of the spigot with an end of the tube. The method further includes slidably inserting the spigot into the tube until the end of the tube contacts a stop surface of the spigot tube coupler. The method also includes forming a plurality of bonding areas between the spigot and the tube, each bonding area defined by an outer surface of the bonding agent within one of the grooves.

Additional features and advantages of the disclosure will be set forth in the description below and, in part, will be apparent from the description or may be learned by practice of the disclosure. The objectives and other advantages of the disclosure will be realized and attained by the structure particularly pointed out in the written description and claims hereof as well as the appended drawings.

It is to be understood that both the foregoing general description and the following detailed description are exemplary and explanatory and are intended to provide further explanation of the disclosure as claimed.

BRIEF DESCRIPTION OF THE DRAWINGS

The accompanying drawings, which are included to provide further understanding of the disclosure and are incorporated in and constitute a part of this specification, illustrate embodiments of the disclosure and together with the description serve to explain the principles of the disclosure.

DETAILED DESCRIPTION

The detailed description set forth below describes various configurations of the subject technology and is not intended to represent the only configurations in which the subject technology may be practiced. The detailed description includes specific details for the purpose of providing a thorough understanding of the subject technology. Accordingly, dimensions are provided in regard to certain aspects as non-limiting examples. However, it will be apparent to those skilled in the art that the subject technology may be practiced without these specific details. In some instances, well-known structures and components are shown in block diagram form in order to avoid obscuring the concepts of the subject technology.

It is to be understood that the present disclosure includes examples of the subject technology and does not limit the scope of the appended claims. Various aspects of the subject technology will now be disclosed according to particular but non-limiting examples. Various embodiments described in the present disclosure may be carried out in different ways and variations, and in accordance with a desired application or implementation.

Figure 1:
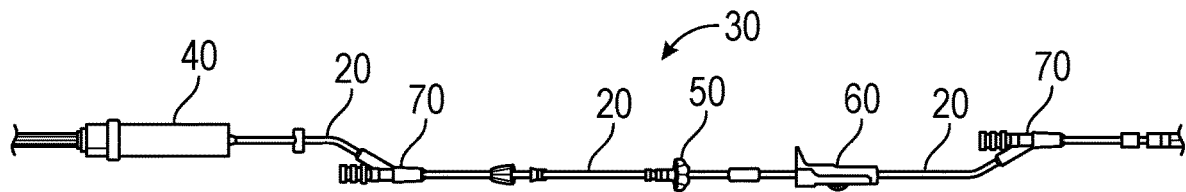
FIG. 1 depicts a schematic view of a typical assembled infusion set.

As shown in FIG. 1, a typical infusion set 30 has several different components, including a drip chamber 40, a check valve 50, a roller clamp 60 and Y-junctions 70, all connected together by tubing 20. A typical infusion set 30 can include additional infusion components (e.g., pinch clamps, filters) and can be formed of any combination of components and the tubing 20.

Figure 2:
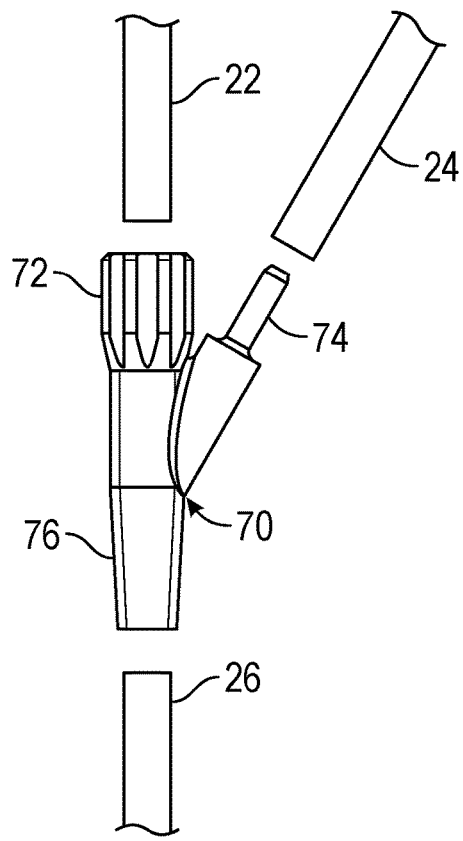
FIG. 2 depicts a schematic view of a typical infusion set component and tubing prior to assembly.

Many of the infusion set components 40, 50, 70 have male connection members or spigots that mate with an end section of tubing 20 to form a connection between the infusion set components 40, 50, 70 and the tubing 20. For example, as shown in FIG. 2, a typical Y-junction 70 has inlet ports 72, 74 and an outlet port 76, where each inlet port 72, 74 is to be connected to an inlet tube 22, 24 and the outlet port 76 is to be connected to an outlet tube 26. Here, the inlet port 74 is a spigot where the inlet tube 24 is to be slid onto and over the inlet port 74 with a tight fit (e.g., friction fit). Typically, because the friction fit alone is not sufficient to ensure the inlet tube 24 stays connected to the inlet port 74, glue or solvent is applied to the outside of the inlet port 74 and then pushed into an end of the inlet tube 24. However, as the inlet tube 24 slides down the smooth surface of the inlet port 74, the tight fit of the inlet tube 24 causes the glue to be pushed down, where it oozes out at the base of the inlet port 74. Because most or all of the glue is essentially scraped off of the smooth surface of the inlet port 74, there may be many areas of the outside surface of the inlet port 74 that have a very thin layer of glue or no glue at all, thus providing little or no additional bond support to the friction fit.

According to aspects of the disclosure, a spigot tube coupler is provided with one or more grooves disposed on the outside surface of the spigot. The grooves provide pockets or recesses where a bonding agent (e.g., glue, solvent) may reside, which prevents all of the bonding agent applied to the spigot from being scraped off as the tube slides onto and down the length of the spigot.

Figure 3:
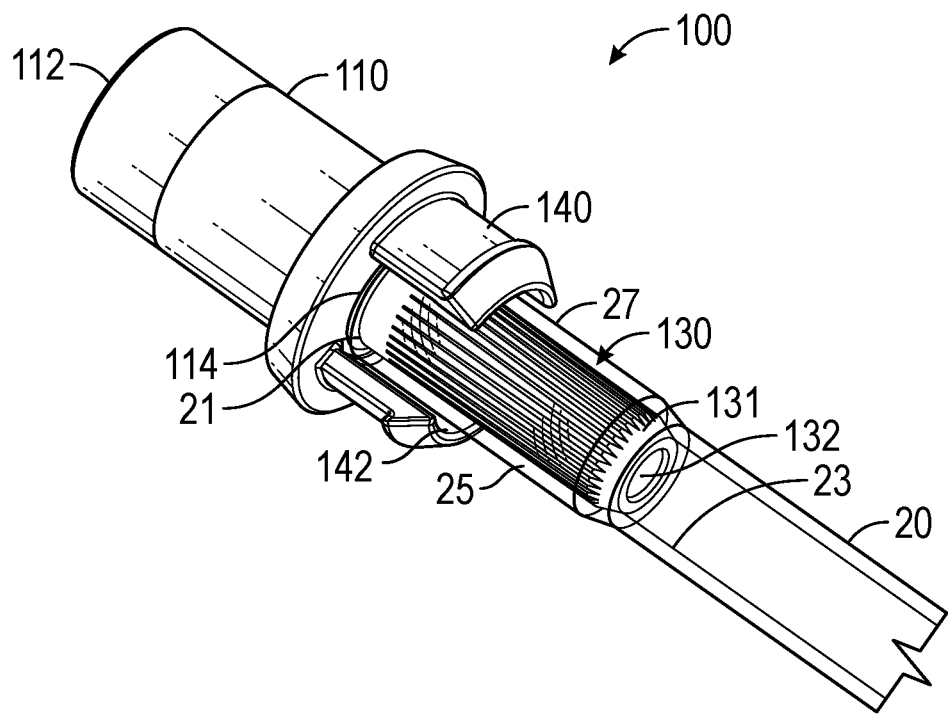
FIG. 3 is a perspective view of an example spigot tube coupler and tube connection, according to some aspects of the disclosure.
Figure 4:
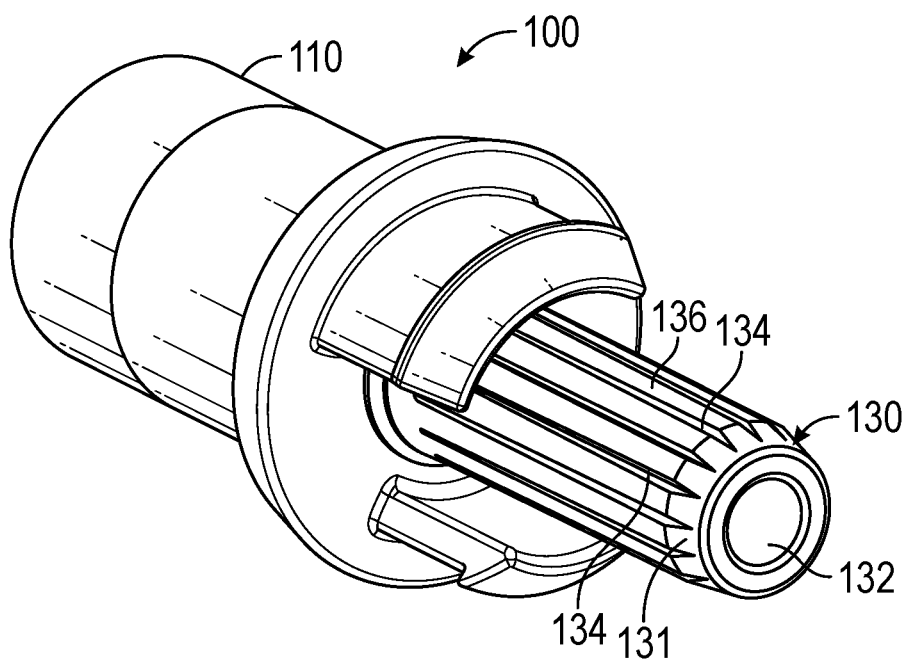
FIG. 4 is a perspective view of an example spigot tube coupler, according to some aspects of the disclosure.
Figure 5:
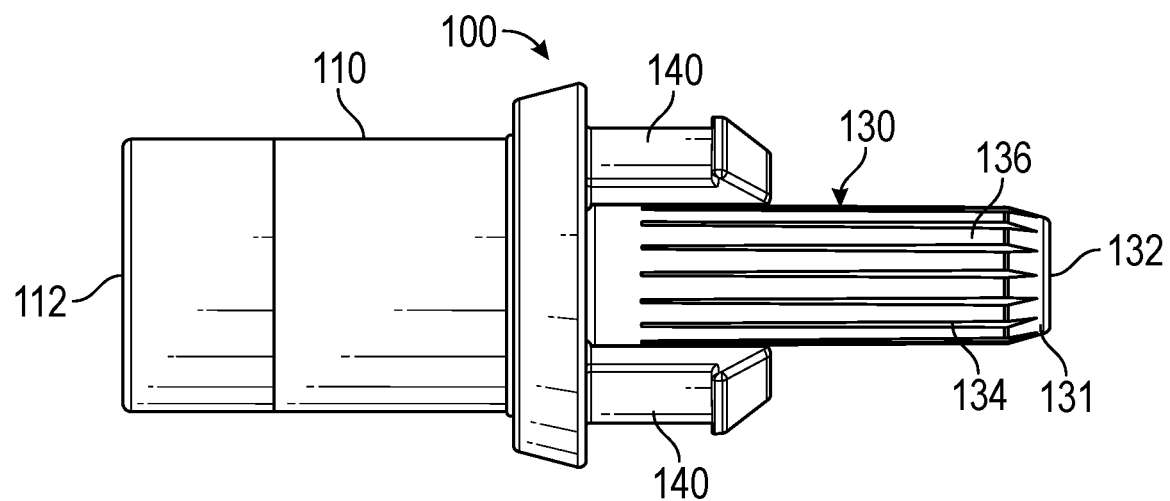
FIG. 5 is a side view of the spigot tube coupler of FIG. 4, according to some aspects of the disclosure.

FIGS. 3-6 illustrate a spigot tube coupler 100, according to some aspects of the disclosure. The spigot tube coupler 100 includes a housing 110, a spigot 130 extending from the housing 110 and sleeve members 140 extending from the housing 110. The housing 110 has a first fluid port 112 configured to provide fluid flow into and out of the housing 110. For example, the first fluid port 112 may be a female connector that receives an end surface of a tube 20 (e.g., tube 22). The spigot 130 has a second fluid port 132 configured to provide fluid flow into and out of the spigot 130. For example, as shown in FIG. 3, the spigot 130 is a male projection that is inserted into a tube 20 (e.g., tube 24) such that fluid can flow into the second fluid port 132 from the tube 20 or flow out of the second fluid port 132 into the tube 20. As seen in FIG. 3, an engagement portion 25 of the tube 20 is the portion of the tube that is mated with the spigot 130, where the engagement portion 25 bulges out due to the friction fit between an inner surface 23 of the tube 20 and the spigot 130. In some aspects of the disclosure, the spigot 130 may be sized the same as the inner surface 23 of the tube 20 for a contact fit, wherein the engagement portion 25 would not bulge out. The spigot 130 may also include a conical portion 131 disposed at the leading edge of the spigot 130. The conical portion 131 may provide a ramped surface to allow the spigot 130 to slide more easily into an end portion 21 of the tube 20.

Figure 6:
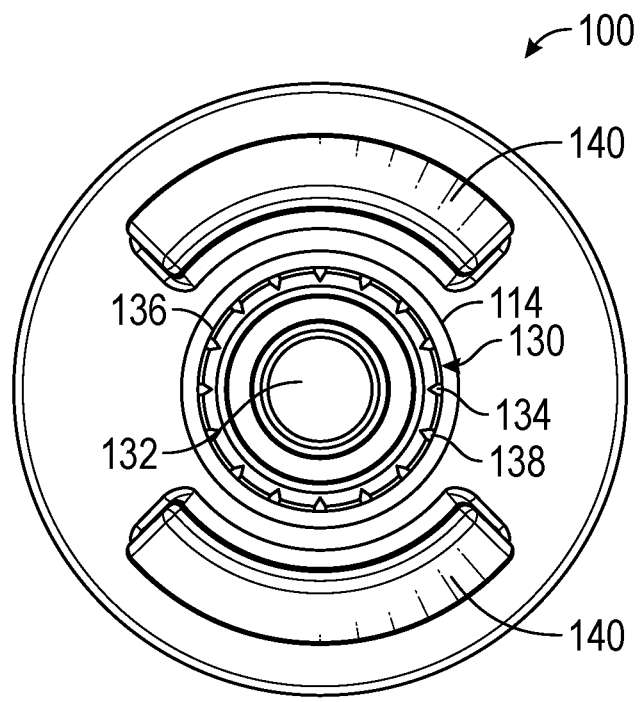
FIG. 6 is a front view of the spigot tube coupler of FIG. 4, according to some aspects of the disclosure.
Figure 10:
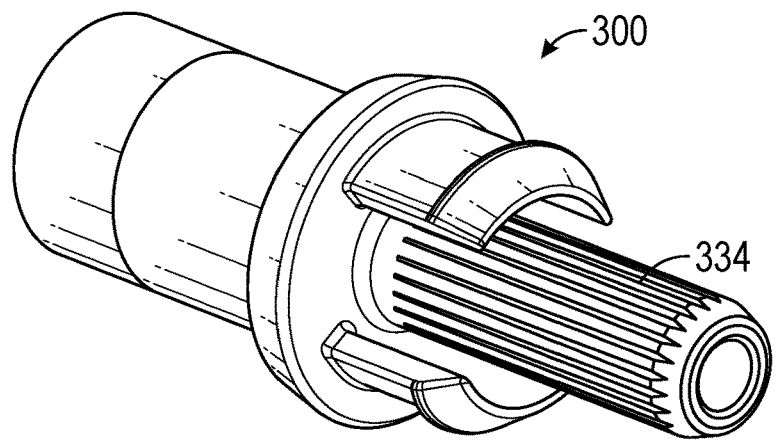
FIG. 10 is a perspective view of an example spigot tube coupler, according to some aspects of the disclosure.
Figure 11:
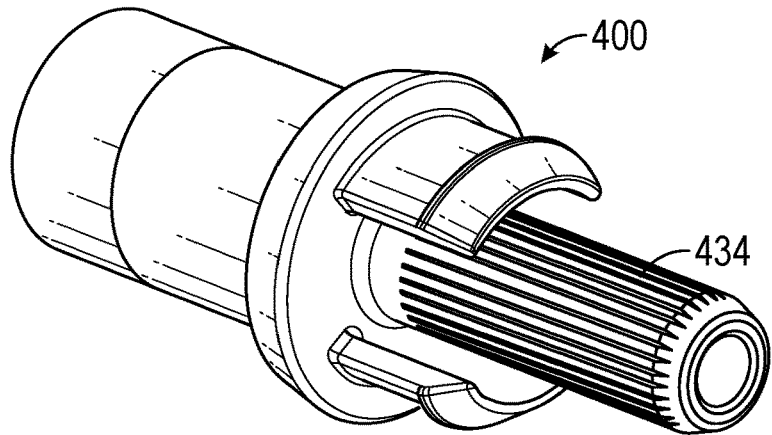
FIG. 11 is a perspective view of an example spigot tube coupler, according to some aspects of the disclosure.
Figure 12:
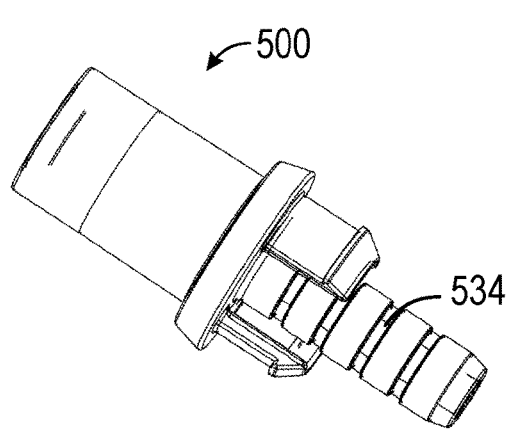
FIG. 12 is a perspective view of an example spigot tube coupler, according to some aspects of the disclosure.
Figure 13:
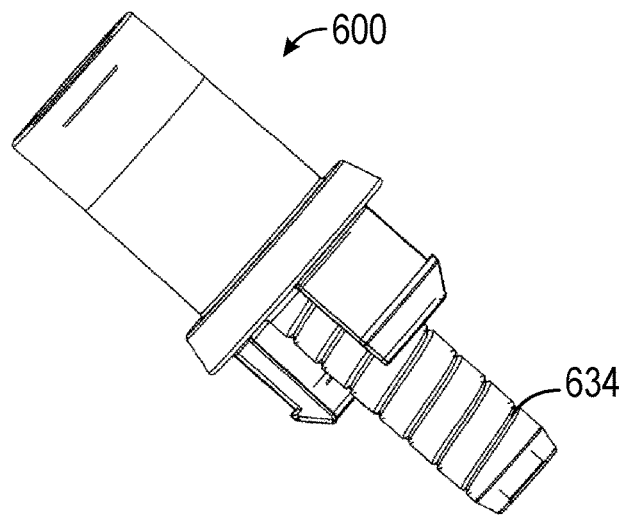
FIG. 13 is a perspective view of an example spigot tube coupler, according to some aspects of the disclosure.

The spigot 130 includes one or more grooves 134 disposed around an outer surface 136 of the spigot 130 (e.g., disposed within the outer surface 136). The grooves 134 may be evenly disposed and/or randomly disposed around the outer surface 136 of the spigot 130. The grooves 134 may be any suitable configuration, such as axial, transverse, helical, or any combination thereof). The grooves 134 are sized and shaped to retain a bonding agent (e.g., glue, solvent), thus providing bonding layers 138 in the outer surface 136 between the tube 20 and the spigot 130. The bonding layers 138 increase the retention strength of the tube 20 connection to the spigot 130 over the friction fit alone. The additional tubing retention strength may be fine-tuned by adjusting parameters of the grooves 134, such as the length of each groove 134, the number of grooves 134 and the geometry of the grooves 134. For example, some or all of the grooves 134 may have a length that essentially matches the length of the spigot 130, or some or all of the grooves 134 may have a length extending along a portion of length of the spigot 130 (e.g., ½ the length of the spigot 130). As another example, the spigot tube coupler 100 of FIGS. 4-6 has 16 grooves 134, the spigot tube coupler 300 shown in FIG. 10 has 24 grooves 334 and the spigot tube coupler 400 shown in FIG. 11 has 32 grooves 434. As further examples, spigot tube coupler 500 shown in FIG. 12 has transverse grooves 534 and spigot tube coupler 600 shown in FIG. 13 has helical grooves 634. As yet another example, while the geometry of the grooves 134 shown in FIG. 6 is triangular, the grooves 134 may have any desirable geometry (e.g., rectangular, semicircular, trapezoidal) or any combination of different geometries (e.g., some triangular and some trapezoidal). In aspects of the disclosure, the grooves 134 may extend into the conical portion 131. In aspects of the disclosure, the grooves 134 may stop before or at the start of the conical portion 131, thus providing the conical portion 131 with a smooth outer surface.

Figure 14:
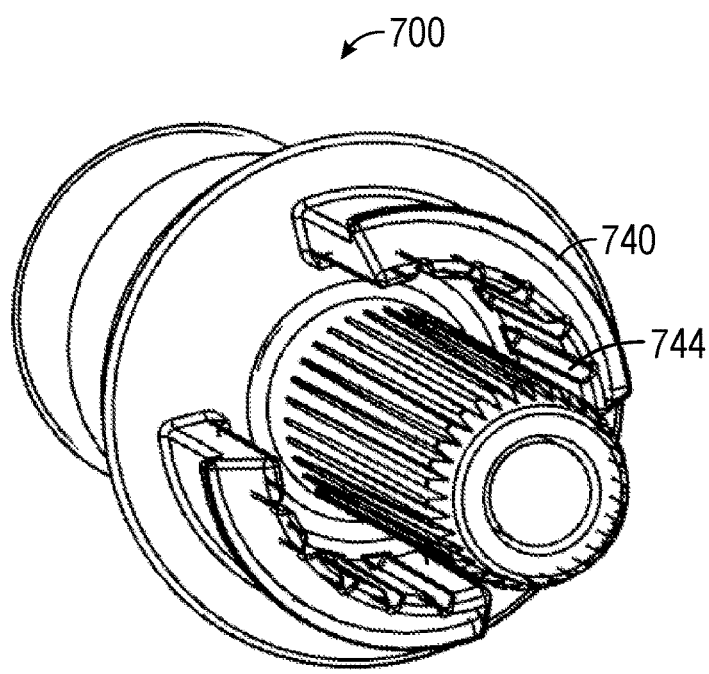
FIG. 14 is a perspective view of an example spigot tube coupler, according to some aspects of the disclosure.

The sleeve members 140 may be configured to partially enclose an end portion 21 of the tube 20. The sleeve members 140 may be configured as a single circular sleeve that encloses the entire end portion 21 of the tube 20. The sleeve members 140 may be configured to not contact an outer surface 27 of the tube 20 as shown in FIG. 3, or the sleeve members 140 may be configured to engage with the outer surface 27 of the tube 20. For example, glue may be applied to an inner surface 142 of the sleeve member 140 to provide another bond layer between the inner surface 142 of the sleeve member 140 and the outer surface 27 of the tube 20, and/or the sleeve member 140 may be configured to provide a tight friction fit between the inner surface 142 of the sleeve member 140 and the outer surface 27 of the tube 20. In some aspects of the disclosure, grooves may be added to the inner surface 142 of the sleeve member 140 to provide similar bonding features as the grooves 134, thus adding bonding layers between the outer surface 27 of the tube 20 and the sleeve members 140 to provide additional bonding strength. For example, spigot tube coupler 700 shown in FIG. 14 has grooves 744 on the sleeve members 740. In some aspects of the disclosure, the grooves 744 may be axial, transverse and/or helical. In some aspects of the disclosure, the spigot tube coupler 100 may have no sleeve member 140 at all.

In assembly, a bonding agent (e.g., glue) is applied to the outer surface 136 of the spigot 130 and the end portion 21 of the tube 20 is slid onto and along the length of the spigot 130 until it contacts a stop surface 114 of the housing 110. The bonding agent that has collected in the grooves 134 then sets to create bonding layers 138 in the outer surface 136 that bond to corresponding portions of the inner surface 23 of the tube 20, providing additional resistance to movement of the tube 20 on the spigot 130 beyond that of the friction fit between the tube 20 and the spigot 130.

Figure 7:
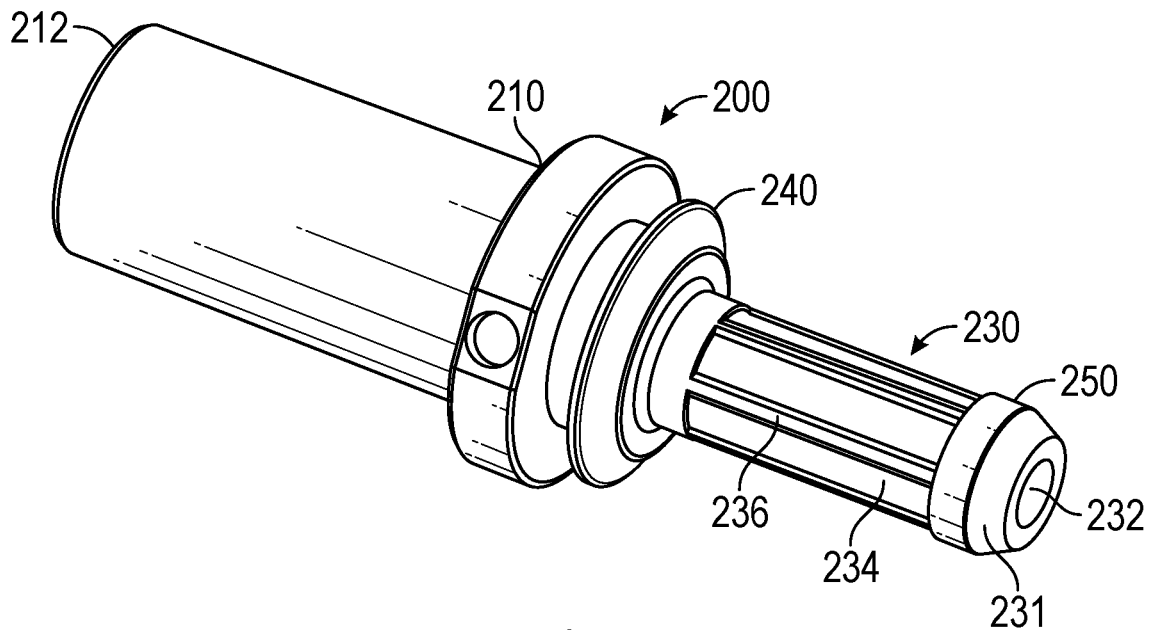
FIG. 7 is a perspective view of an example spigot tube coupler, according to some aspects of the disclosure.
Figure 8:
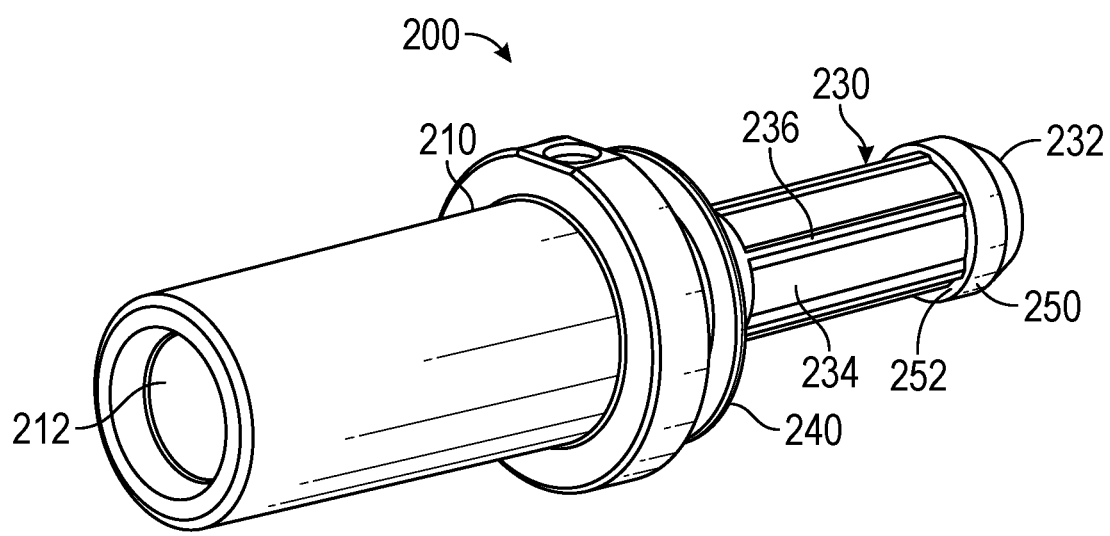
FIG. 8 is another perspective view of spigot tube coupler of FIG. 7, according to some aspects of the disclosure.
Figure 9:
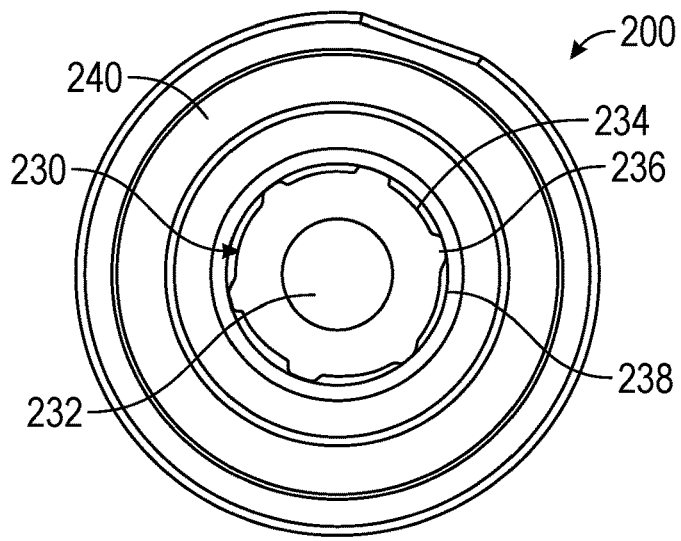
FIG. 9 front view of the spigot tube coupler of FIG. 7, according to some aspects of the disclosure.

FIGS. 7-9 illustrate a spigot tube coupler 200, according to some aspects of the disclosure. The spigot tube coupler 200 includes a housing 210, a base member 240 extending from the housing 210 and a spigot 230 extending from the base member 240. The housing 210 has a first fluid port 212 configured to provide fluid flow into and out of the housing 210. For example, the first fluid port 212 may be a female connector that receives an end surface of a tube 20 (e.g., tube 22). The spigot 230 has a second fluid port 232 configured to provide fluid flow into and out of the spigot 230. For example, as shown in FIGS. 7-9, the spigot 230 is a male projection that is configured to be inserted into a tube 20 (e.g., tube 24) such that fluid can flow into the second fluid port 232 from the tube or flow out of the second fluid port 232 into the tube.

The spigot 230 includes one or more grooves 234 (e.g., channels) disposed around an outer surface 236 of the spigot 230. The grooves 234 are sized and shaped to retain a bonding agent (e.g., glue, solvent), thus providing bonding layers 238 in the outer surface 236 between the tube (e.g., tube 20) and the spigot 230. The bonding layers 238 increase the retention strength of the tube connection to the spigot 230 over a friction fit alone. The additional tubing retention strength may be fine-tuned by adjusting parameters of the grooves 234, such as the length of each groove 234, the number of grooves 234 and the geometry of the grooves 234. For example, some or all of the grooves 234 may have a length that essentially matches the length of the spigot 230, or some or all of the grooves 234 may have a length extending along a portion of length of the spigot 230 (e.g., ½ the length of the spigot 230). As another example, while the spigot tube coupler 200 of FIGS. 7-9 has 6 grooves 234, the spigot tube coupler 200 may have any number of grooves. As yet another example, while the geometry of the grooves 234 shown in FIG. 9 is essentially trapezoidal, the grooves 234 may have any desirable geometry (e.g., rectangular, semicircular, triangular).

The spigot 230 also includes a collar 250 disposed adjacent the second fluid port 232. The collar 250 may be sized and shaped to extend radially outward past the outer surface 236 of the spigot 230, thus providing a retention wall 252. The retention wall 252 provides a retention surface to help hold the bonding agent in the grooves 234 during application of the bonding agent and during assembly of the spigot tube coupler 200. The collar 250 may be configured to provide a greater friction fit with the tube 20 than the friction fit between the outer surface 236 of the spigot 230 and the tube 20. Further, the collar 250 may function as a barb of sorts, thereby providing additional resistance to movement of the tube 20 once the tube 20 is mated to the spigot 230. The spigot 230 may also include a conical portion 231 disposed at the leading edge of the spigot 230. The conical portion 231 provides a ramped surface to allow the spigot 230 to slide more easily into an end portion 21 of the tube 20. The size of the collar 250 (e.g., the outer diameter) may be configured to provide a desired level of glue retention and barbed resistance. While not shown in FIGS. 7-9, the spigot tube coupler 200 may also include a sleeve member as described above in relation to spigot tube coupler 100. In aspects of the disclosure, the grooves 234 stop at the retention wall 252 of the collar 250 and before the start of the conical portion 231, thus providing the conical portion 231 with a smooth outer surface. In aspects of the disclosure, the grooves 234 may extend into the conical portion 231. For example, the collar 250 may be disposed around the outer surface 236 of the spigot 230 and the grooves 234 may extend under the collar 250 and into the conical portion 231.

Any or all of the elements of the above described spigot tube couplers 100, 200, 300, 400, 500, 600, 700 may be utilized on any device (e.g., a pump tube connector, tube connectors of infusion set components 40, 50, 70). For example, the inlet port 74 of Y-junction 70 shown in FIG. 2 may be provided as spigot 130, spigot 230 or the spigots of any of spigot tube couplers 300, 400, 500, 600, 700, thereby providing the corresponding increased retention features as described. Similarly, any male projection of an infusion device, such as an infusion pump or an infusion set component, which is intended to mate with a tube end (e.g., end portion 21) may be configured or provided as spigot 130, spigot 230 or the spigots of any of spigot tube couplers 300, 400, 500, 600, 700.

In one or more embodiments of the disclosure, a spigot tube coupler comprises a housing comprising a first fluid port disposed at a first end of the housing and a stop surface disposed at a second end of the housing. The spigot tube coupler also comprises a spigot extending from the stop surface and configured to be inserted into a tube. The spigot comprises an insertion end, a second fluid port disposed at the insertion end, an outer surface and one or more grooves disposed around the outer surface, wherein the one or more grooves are configured to receive a bonding agent to provide one or more bonding layers between the spigot and the tube.

In aspects of the disclosure, a sleeve member extends from the stop surface of the housing and at least partially encircles a portion of the spigot, the sleeve member configured to be disposed at least partially around an end portion of the tube. In aspects of the disclosure, the outer surface of the spigot comprises an outer diameter that is one of equal to and larger than an inner diameter of the tube to provide a friction fit between the spigot and the tube. In aspects of the disclosure, the one or more grooves comprises a plurality of grooves spaced evenly around the outer surface of the spigot. In aspects of the disclosure, the plurality of grooves comprises one of 16, 24 and 32 grooves. In aspects of the disclosure, the one or more grooves are triangular shaped. In aspects of the disclosure, the one or more grooves are semi-circular shaped. In aspects of the disclosure, the one or more grooves are one of trapezoidal shaped and rectangular shaped. In aspects of the disclosure, the one or more grooves are one of axial grooves, transverse grooves and helical grooves.

In aspects of the disclosure, the spigot comprises a conical portion disposed at the insertion end, the conical portion configured to provide a ramped surface to be initially inserted into the tube. In aspects of the disclosure, the one or more grooves extend into the conical portion. In aspects of the disclosure, the stop surface of the housing comprises a base member extending from the housing. In aspects of the disclosure, a collar is disposed at the insertion end of the spigot, the collar having an outer diameter greater than the outer surface of the spigot. In aspects of the disclosure, the collar comprises a retention wall defining an end to each of the one or more grooves, the retention wall configured to contain the bonding agent within the one or more grooves. In aspects of the disclosure, the spigot comprises a conical portion disposed past the collar at the insertion end, the conical portion configured to provide a ramped surface to be initially inserted into the tube.

In one or more embodiments of the disclosure, a spigot tube coupler comprises a stop surface and a spigot extending from the stop surface and configured to be inserted into a tube. The spigot comprises an insertion end, a fluid port disposed in the center of the spigot, an outer surface and a plurality of grooves disposed around the outer surface, wherein the plurality of grooves are configured to receive a bonding agent to provide a plurality of bonding areas between the spigot and the tube.

In aspects of the disclosure, the spigot comprises a conical portion disposed at the insertion end, the conical portion configured to provide a ramped surface to be initially inserted into the tube. In aspects of the disclosure, a collar is disposed adjacent to the conical portion, the collar having an outer diameter greater than the outer surface of the spigot, wherein the collar comprises a retention wall defining an end to each of the plurality of grooves, the retention wall configured to contain the bonding agent within the plurality of grooves.

In one or more embodiments of the disclosure, a method of assembling a spigot tube coupler and a tube comprises applying a bonding agent to an outer surface of a spigot of a spigot tube coupler, the spigot comprising a plurality of grooves disposed around the outer surface; aligning an insertion end of the spigot with an end of the tube; slidably inserting the spigot into the tube until the end of the tube contacts a stop surface of the spigot tube coupler; and forming a plurality of bonding areas between the spigot and the tube, each bonding area defined by an outer surface of the bonding agent within one of the grooves.

In aspects of the disclosure, the method comprises applying the bonding agent to the outer surface of the spigot between a collar disposed on the insertion end of the spigot and the stop surface of the spigot tube coupler, the collar comprising an outer diameter greater than the outer surface of the spigot and a retention wall defining an end to each of the plurality of grooves; and generating a friction fit between the collar and an inner surface of the tube.

It is understood that any specific order or hierarchy of blocks in the methods of processes disclosed is an illustration of example approaches. Based upon design or implementation preferences, it is understood that the specific order or hierarchy of blocks in the processes may be rearranged, or that all illustrated blocks be performed. In some implementations, any of the blocks may be performed simultaneously.

The present disclosure is provided to enable any person skilled in the art to practice the various aspects described herein. The disclosure provides various examples of the subject technology, and the subject technology is not limited to these examples. Various modifications to these aspects will be readily apparent to those skilled in the art, and the generic principles defined herein may be applied to other aspects.

A reference to an element in the singular is not intended to mean "one and only one" unless specifically so stated, but rather "one or more." Unless specifically stated otherwise, the term "some" refers to one or more. Pronouns in the masculine (e.g., his) include the feminine and neuter gender (e.g., her and its) and vice versa. Headings and subheadings, if any, are used for convenience only and do not limit the invention.

The word "exemplary" is used herein to mean "serving as an example or illustration." Any aspect or design described herein as "exemplary" is not necessarily to be construed as preferred or advantageous over other aspects or designs. In one aspect, various alternative configurations and operations described herein may be considered to be at least equivalent.

As used herein, the phrase "at least one of" preceding a series of items, with the term "or" to separate any of the items, modifies the list as a whole, rather than each item of the list. The phrase "at least one of" does not require selection of at least one item; rather, the phrase allows a meaning that includes at least one of any one of the items, and/or at least one of any combination of the items, and/or at least one of each of the items. By way of example, the phrase "at least one of A, B, or C" may refer to: only A, only B, or only C; or any combination of A, B, and C.

A phrase such as an "aspect" does not imply that such aspect is essential to the subject technology or that such aspect applies to all configurations of the subject technology. A disclosure relating to an aspect may apply to all configurations, or one or more configurations. An aspect may provide one or more examples. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples. A phrase such an embodiment may refer to one or more embodiments and vice versa. A phrase such as a "configuration" does not imply that such configuration is essential to the subject technology or that such configuration applies to all configurations of the subject technology. A disclosure relating to a configuration may apply to all configurations, or one or more configurations. A configuration may provide one or more examples. A phrase such a configuration may refer to one or more configurations and vice versa.

In one aspect, unless otherwise stated, all measurements, values, ratings, positions, magnitudes, sizes, and other specifications that are set forth in this specification, including in the claims that follow, are approximate, not exact. In one aspect, they are intended to have a reasonable range that is consistent with the functions to which they relate and with what is customary in the art to which they pertain.

It is understood that the specific order or hierarchy of steps, operations or processes disclosed is an illustration of exemplary approaches. Based upon design preferences, it is understood that the specific order or hierarchy of steps, operations or processes may be rearranged. Some of the steps, operations or processes may be performed simultaneously. Some or all of the steps, operations, or processes may be performed automatically, without the intervention of a user. The accompanying method claims, if any, present elements of the various steps, operations or processes in a sample order, and are not meant to be limited to the specific order or hierarchy presented.

All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112 (f) unless the element is expressly recited using the phrase "means for" or, in the case of a method claim, the element is recited using the phrase "step for." Furthermore, to the extent that the term "include," "have," or the like is used, such term is intended to be inclusive in a manner similar to the term "comprise" as "comprise" is interpreted when employed as a transitional word in a claim.

The Title, Background, Summary, Brief Description of the Drawings and Abstract of the disclosure are hereby incorporated into the disclosure and are provided as illustrative examples of the disclosure, not as restrictive descriptions. It is submitted with the understanding that they will not be used to limit the scope or meaning of the claims. In addition, in the Detailed Description, it can be seen that the description provides illustrative examples and the various features are grouped together in various embodiments for the purpose of streamlining the disclosure. This method of disclosure is not to be interpreted as reflecting an intention that the claimed subject matter requires more features than are expressly recited in each claim. Rather, as the following claims reflect, inventive subject matter lies in less than all features of a single disclosed configuration or operation. The following claims are hereby incorporated into the Detailed Description, with each claim standing on its own as a separately claimed subject matter.

The claims are not intended to be limited to the aspects described herein, but are to be accorded the full scope consistent with the language claims and to encompass all legal equivalents. Notwithstanding, none of the claims are intended to embrace subject matter that fails to satisfy the requirement of 35 U.S.C. § 101, 102, or 103, nor should they be interpreted in such a way.

The invention claimed is:

1. A spigot tube coupler, comprising:
    a housing comprising:
        a first fluid port disposed at a first end of the housing; and
        a stop surface disposed at a second end of the housing; and
    a spigot extending from the stop surface and configured to be inserted into a tube, the spigot comprising:
        an insertion end;
        a second fluid port disposed at the insertion end;
        an outer surface;
        a collar disposed at the insertion end of the spigot, the collar having an outer diameter greater than the outer surface of the spigot and the outer surface having a continuous diameter between the stop surface and the collar; and
        one or more grooves disposed around the outer surface, wherein the one or more grooves are configured to receive a bonding agent to provide one or more bonding layers between the spigot and the tube, wherein the collar comprises a retention wall defining an end to each of the one or more grooves that extend to the collar, the retention wall configured to contain the bonding agent within the one or more grooves.

2. The spigot tube coupler of claim 1, further comprising a sleeve member extending from the stop surface of the housing and at least partially encircling a portion of the spigot, the sleeve member configured to be disposed at least partially around an end portion of the tube.

3. The spigot tube coupler of claim 1, wherein the outer surface of the spigot comprises an outer diameter that is one of equal to and larger than an inner diameter of the tube to provide a friction fit between the spigot and the tube.

4. The spigot tube coupler of claim 1, wherein the one or more grooves comprises a plurality of grooves spaced evenly around the outer surface of the spigot.

5. The spigot tube coupler of claim 1, wherein the one or more grooves are disposed axially along the outer surface.

6. The spigot tube coupler of claim 5, wherein the one or more grooves are trapezoidal shaped.

7. The spigot tube coupler of claim 5, wherein the one or more grooves are rectangular shaped.

8. The spigot tube coupler of claim 1, wherein the one or more grooves are disposed transversely along the outer surface.

9. The spigot tube coupler of claim 1, wherein the one or more grooves are disposed helically along the outer surface.

10. The spigot tube coupler of claim 1, wherein the spigot comprises a conical portion disposed at the insertion end, the conical portion configured to provide a ramped surface to be initially inserted into the tube.

11. The spigot tube coupler of claim 10, wherein the one or more grooves extend into the conical portion.

12. The spigot tube coupler of claim 1, wherein the stop surface of the housing comprises a base member extending from the housing.

13. The spigot tube coupler of claim 12, wherein the outer surface of the spigot has a continuous diameter between the base member and the collar.

14. A spigot tube coupler, comprising:
    a stop surface having a base member; and
    a spigot extending from the base member and configured to be inserted into a tube, the spigot comprising:
        an insertion end;
        a fluid port disposed in the center of the spigot;
        an outer surface;
        a collar disposed at the insertion end of the spigot, the collar having an outer diameter greater than the outer surface of the spigot and the outer surface having a continuous diameter between the base member and the collar; and
        a plurality of grooves disposed around the outer surface, wherein the plurality of grooves are configured to receive a bonding agent to provide a plurality of bonding areas between the spigot and the tube, wherein the collar comprises a retention wall defining an end to each of the plurality of grooves, the retention wall configured to contain the bonding agent within the plurality of grooves.

15. The spigot tube coupler of claim 14, wherein the spigot comprises a conical portion disposed at the insertion end, the conical portion configured to provide a ramped surface to be initially inserted into the tube.

16. A method of assembling a spigot tube coupler and a tube, the method comprising:
    applying a bonding agent to an outer surface of a spigot of a spigot tube coupler, the spigot comprising a plurality of grooves disposed around the outer surface, the outer surface having a continuous diameter between a stop surface of the spigot tube coupler and a collar disposed at an insertion end of the spigot;
    aligning the insertion end of the spigot with an end of the tube;

slidably inserting the spigot into the tube until the end of the tube contacts the stop surface of the spigot tube coupler; and forming a plurality of bonding areas between the spigot and the tube, each bonding area defined by an outer surface of the bonding agent within one of the grooves, wherein the collar comprises a retention wall defining an end to each of the plurality of grooves that extends to the collar, the retention wall containing the bonding agent within the one or more grooves during the steps of applying the bonding agent and inserting the spigot into the tube.

17. The method of claim 16, further comprising:

applying the bonding agent to the outer surface of the spigot between the collar and the stop surface of the spigot tube coupler, the collar comprising an outer diameter greater than the outer surface of the spigot; and generating a friction fit between the collar and an inner surface of the tube.

\* \* \* \* \*